(12) United States Patent
Rossant et al.

(10) Patent No.: US 6,630,349 B1
(45) Date of Patent: Oct. 7, 2003

(54) TROPHOBLAST CELL PREPARATIONS

(75) Inventors: Janet Rossant, Toronto (CA); Satoshi Tanaka, Tokyo (JP); Tilo Kunath, Toronto (CA)

(73) Assignee: Mount Sinai Hospital, Toronto (CA)

( * ) Notice: Subject to any disclaimer, the term of this patent is extended or adjusted under 35 U.S.C. 154(b) by 0 days.

(21) Appl. No.: 09/786,585

(22) PCT Filed: Sep. 23, 1999

(86) PCT No.: PCT/CA99/00867

§ 371 (c)(1), (2), (4) Date: Mar. 7, 2001

(87) PCT Pub. No.: WO00/17325

PCT Pub. Date: Mar. 30, 2000

Related U.S. Application Data

(60) Provisional application No. 60/101,483, filed on Sep. 23, 1998.

(51) Int. Cl.$^7$ ............................. C12N 5/02; C12N 5/00; C12N 15/85; C12N 15/00
(52) U.S. Cl. ....................... 435/325; 435/373; 435/377; 435/455; 800/21
(58) Field of Search ................................ 435/325, 455, 435/373, 377; 800/21

(56) References Cited

U.S. PATENT DOCUMENTS

| | | | |
|---|---|---|---|
| 5,670,372 A | | 9/1997 | Hogan |
| 5,942,435 A | * | 8/1999 | Wheeler ...................... 435/325 |
| 6,200,806 B1 | * | 3/2001 | Thomson ..................... 435/366 |

FOREIGN PATENT DOCUMENTS

WO   WO96/22362 A1   7/1996

OTHER PUBLICATIONS

IL Weissman, Science, "Translating Stem and Progenitor Cell Biology to the Clinic: Barriers and Opportunities," Feb. 2000, vol. 287, pp. 1442–1446.*
PJ Donovan et al., Nature, "The end of the beginning for pluripotent stem cells," Nov. 2001, vol. 414, pp. 92–97.*
GP Hamlin et al., Endocrinology, "Regulation of Deoxyribonucleic Acid Synthesis in Proliferating and Differentiating Trophoblast Cells: Involvement of Transferrin, Transforming Growth Factor–Beta, and Tyrosine Kinases," Jan. 1995, vol. 136, No. 1, pp. 322–331.*
J. Rossant, "Development of Extraembryonic Cell Lineages in the Mouse Embryo", in Experimental Approaches to Early Mammalian Development, ed. J. Rossant et al, pp. 97–120, Cambridge University Press, London (1986).
J. Rossant, "Development of the Extraembryonic Lineages", Seminars in Development Biology, 6:237–247 (1995).
J. Rossant et al, "Investigation of the Potency of Cells from the Postimplantation Mouse Embryo by Blastocyts Injection: a Preliminary Report", J. Embryol. Exp. Morph. 48:239–247 (1978).

M. Johnson et al, "Molecular Studies on Cells of the Trophectodermal Lineage of the Postimplantation Mouse Embryo", J. Embryol. Exp. Morph., 61:103–116 (1981).

R. Gardner, "An Investigation of Inner Cell Mass and Trophoblast Tissues Following Their Isolation from the mouse Blastocyst", J. Embryol. Exp. Morph., 28(2):279–312 (1972).

J. Rossant et al, "Effect of Culture Conditions on Diploid to Giant–Cell Transformation in Postimplantation Mouse Trophoblast", J. Embryol. Exp. Morph., 62:217–227 (1981).

E. Ilgren, "Review Article: Control of Trophoblastic Growth", Placenta, 4:307–328 (1983).

J. Rossant et al, "Propeties of Extra–Embryonic Ectoderm Isolated from Postimplantation Mouse Embryos", J. Embryol. Exp. Morph., 39:183–194 (1977).

E. Ilgren, "On the Control of the Trophoblastic Giant–Cell Transformation in the Mouse: Homotypic Cellular Interactions and Polyploidy", J. Embryol. Exp. Morph., 62:183–202 (1981).

L. Niswander et al, "Fgf–4 Expression During Gastrulation, Myogenesis, Limb and Tooth Development in the Mouse", Development, 114:755–768 (1992).

D. Rappolee et al, "Expression and Function of FGF–4 in Peri–implantation Development in Mouse Embryos", Development, 120:2259–2269 (1994).

A. Orr–Urtreger et al, "Developmental Localization of the Splicing Alternatives of Fibroblast Growth Factor Receptor–2 (FGFR2)", Developmental Biology, 158:475–486 (1993).

E. Arman et al, "Targeted Disruption of Fibroblast Growth Factor (FGF) Receptor 2 Suggests a Role for FGF Signaling in Pregastrulation Mammalian Development", Proc. Natl. Acad. Sci. USA, 95:5082–5087 (Apr., 1998).

B. Feldman et al, "Requirement of FGF–4 for Postimplantation Mouse Development", Science, 267:246–249 (Jan. 1995).

N. Chai et al, "FGF is an Essential Regulator of the Fifth Cell Division in Preimplantation Mouse Embryos", Developmental Biology, 198:105–115 (1998).

(List continued on next page.)

Primary Examiner—Anne M. Wehbe'
Assistant Examiner—Q Janice Li
(74) Attorney, Agent, or Firm—Howson and Howson

(57) ABSTRACT

Stable pluripotent trophoblast stem (TS) cell lines and uses of the cell lines are described. The cell lines comprise cells that (i) are capable of indefinite proliferation in vitro in an undifferentiated state, and (ii) are capable of differentiation into cells of the trophoblast lineage in vivo.

16 Claims, 4 Drawing Sheets

OTHER PUBLICATIONS

B. Hogan et al, "Manipulating the Mouse Embryo", Cold Spring Harbor Laboratory Press, $2^{nd}$ ed., pp. 265–272, Cold Spring Harbor, New York (1994).

E. Robertson et al, "Embryo–derived Stem Cell Lines", in Teratocarcinomas and Embryonic Stem Cells, Chapter 4, pp. 71–112, ed. E. Robertson, JRL Press, Oxford (1987).

J.–E. Flechon et al, "Isolation and Characterization of a Feeder–dependent, Porcine Trophectoderm Cell Line Obtained from a 9–Day Blastocyst", Placenta, 16:643–658 (1995).

K. Pettersson et al, "Expression of a Novel Member of Estrogen Response Element–Binding Nuclear Receptors is Restricted to the Early Stages of Chorion Formation During Mouse Embryogenesis", Mechanisms of Development, 54:211–223 (1996).

J. Luo et al, "Placental Abnormalities in Mouse Embryos Lacking the Orphan Nuclear Receptor ERR–β", Nature, 388:778–782 (Aug., 1997).

F. Beck et al, "Expression of Cdx–2 in the Mouse Embryo and Placenta: Possible Role in Patterning of the Extra–Embryonic Membranes", Developmental Dynamics 204:219–227 (1995).

B. Ciruna et al, "Gene Expression Patter, Expression of the T–box Gene Eomesodermin During Early Mouse Development", Mechanisms of Development, 81:199–203 (1999).

K. Lescisin et al, "Isolation and Characterization of a Novel Trophoblast–specific cDNA in the Mouse", Genes and Development, 2:1639–1646 (1988).

F. Guillemot et al, "Essential Role of Mash–2 in Extraembryonic Development", Nature, 371:333–336 (Sep., 1994).

M. Tanaka et al, "Mash2 Acts Cell Autonomously in Mouse Spongiotrophoblast Development", Developmental Biology 190:55–65 (1997).

T. Faria et al, "Localization of Placental Lactogen–I in Trophoblast Giant Cells of the Mouse Placenta", Biology of Reproduction, 44:327–331 (1991).

J. Cross et al, "Hxt Encodes a Basic Helix–Loop–Helix Transcription Factor that Regulates Trophoblast Cell Development", Development 121:2513–2523 (1995).

P. Riley et al, "The Hand1 bHLH Transcription Factor is Essential for Placentation and Cardiac Morphogenesis", Nature Genetics, 18:271–275 (Mar., 1998).

S. Palmieri et al, "Oct–4 Transcription Factor is Differentially Expressed in the Mouse Embryo During Establishment of the First Two Extraembryonic Cell Lineages Involved in Implantation", Developmental Biology, 166:259–267 (1994).

H. Scholer et al, "Oct–4: a Germline–specific Transcription Factor Mapping to the Mouse t–complex", EMBO J., 9(7):2185–2195 (1990).

D. Wilkinson et al, "Expression Pattern of the Mouse T Gene and its Role in Mesoderm Formation", Nature, 343:657–659 (Feb., 1990).

S. Wood et al, "Non–Injection Methods for the Production of Embryonic Stem Cell–Embryo Chimaeras", Nature, 365:87–89 (Sep., 1993).

S. Duncan et al, "Expression of Transcription Factor HNF–4 in the Extraembryonic Endoderm, Gut, and Nephrogenic Tissue of the Developing Mouse Embryo: HNF–4 is a Marker for Primary Endoderm in the Implanting Blastocyst", Proc. Natl. Acad. Sci. USA, 91:7598–7602 (Aug., 1994).

A–K. Hadjantonakis et al, "Generating Green Fluorescent Mice by Germline Transmission of Green Fluorescent ES Cells", Mechanisms of Development, 76:79–90 (1998).

K. Griffin et al, "Molecular Identification of Spadetail: Regulation of Zebrafish Trunk and Tail Mesoderm Formation by T–box Genes", Development, 125:3379–3388 (1998).

K. Griffin et al, "Analysis of FGF Function in Normal and No Tail Zebrafish Embryos Reveals Separate Mechanisms for Formation of the Trunk and the Tail", Development, 121:2983–2994 (1995).

M. Pownall et al, "Two Phases of Hox Gene Regulation During Early Xenopus Development", Current Biology, 8:673–676 (1998).

H. Isaacs et al, "Regulation of Hox Gene Expression and Posterior Development by the Xenopus caudal Homologue Xcad3", EMBO J., 17(12):3413–3427 (1998).

C. Stewart et al, "Expression of Retroviral Vectors in Transgenic Mice Obtained by Embryo Infection", EMBO J., 6(2):383–388 (1987).

R. Heim et al, "Wavelength Mutations and Posttranslational Autoxidation of Green Fluorescent Protein", Proc. Natl. Acad. Sci. USA, 91:12501–12504 (Dec., 1994).

M. Zernicka–Goetz et al, "Following Cell Fate in the Living Mouse Embryo", Development, 124:1133–1137 (1997).

M. Okabe et al, "Green Mice as a Source of Ubiquitous Green Cells", FEBS Letters, 407:313–319 (1997).

D. Hill et al, "Screening for Novel Pattern Formation Genes Using Gene Trap Approaches", Methods in Enzymology, 225:664–681 (1993).

H. Van Der Putten et al, "Efficient Insertion of Genes into the Mouse Germ Line Via Retroviral Vectors", Proc. Natl. Acad. Sci. USA, 82:6148–6152 (Sep., 1985).

Andras Nagy et al, "Production of Completely ES Cell–Derived Fetuses", Gene Targeting: A Practical Approach, A. Joyner ed., pp. 147–179 (1993).

Wolfgang Wurst et al, "Production of Targeted Embryonic Stem Cell Clones", Gene Targeting, A. Joyner ed., IRL Press, pp. 33–61 (1993).

H. Nakayama, The Transition to Endoreduplication in Trohoblast Giant Cells is Regulated by the mSNA Zinc Finger Transcription Factor, Development Biology, 199, 150–163 (Jul. 1, 1998).

\* cited by examiner

Fig. 1A
Fig. 1B
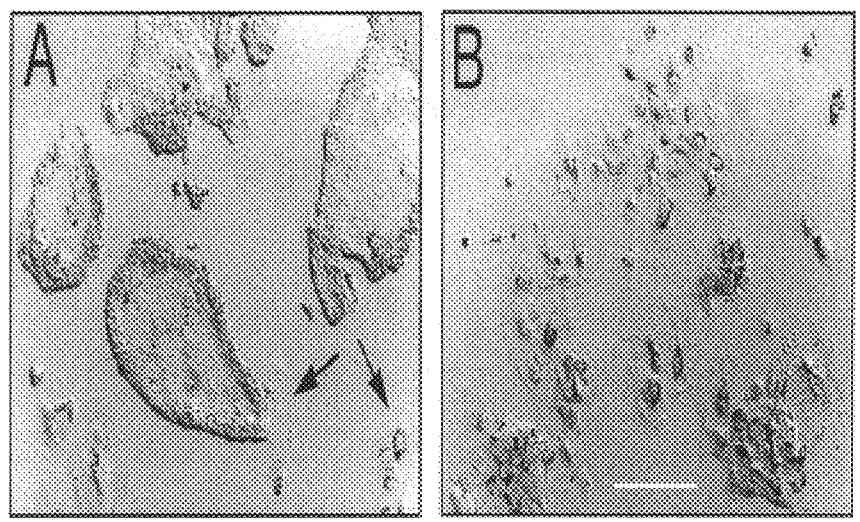
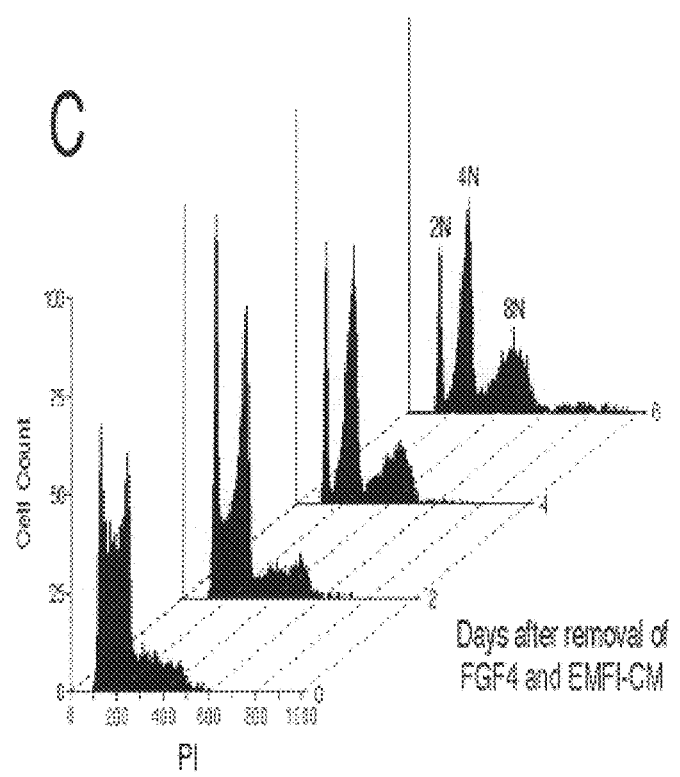
Fig. 1C

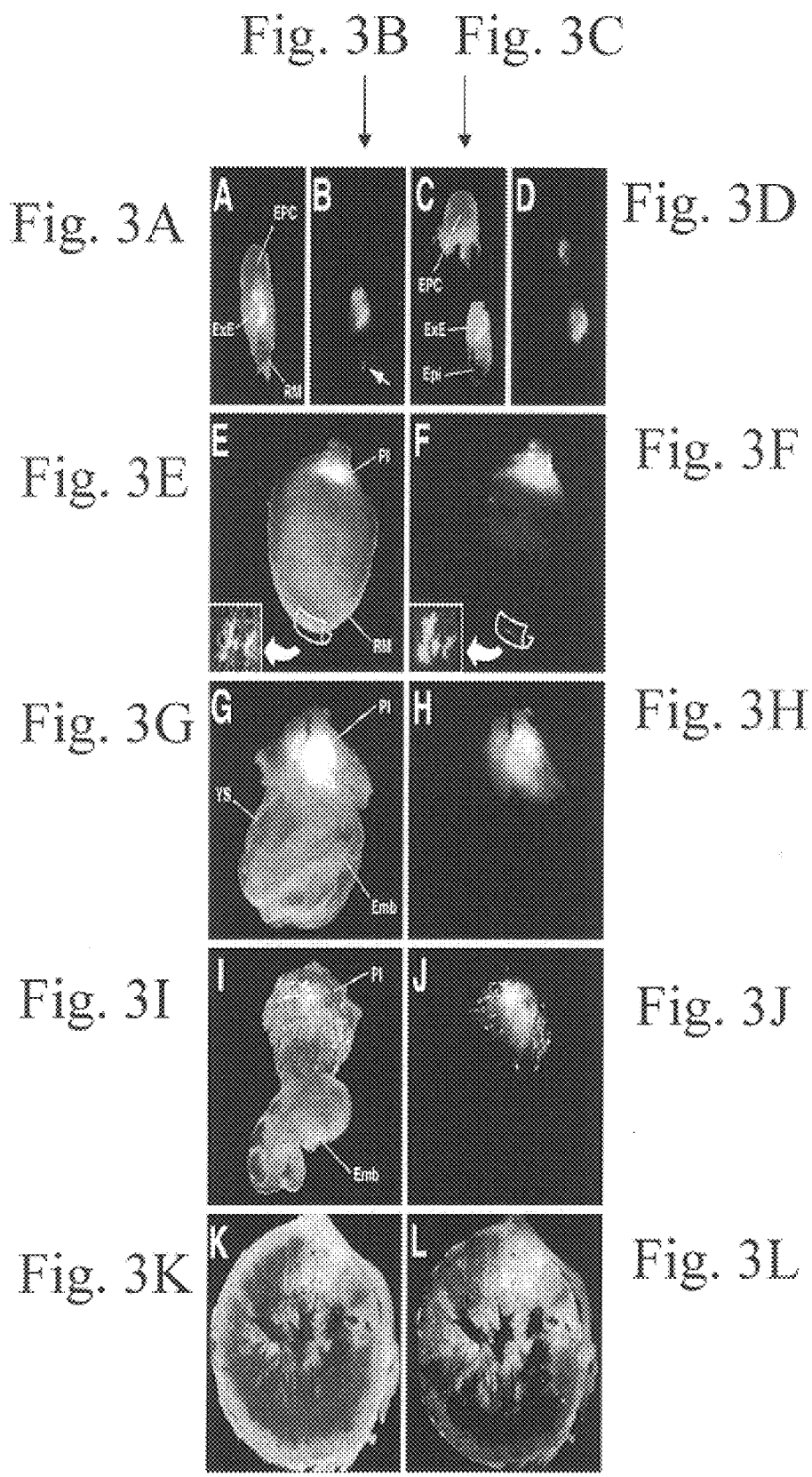

TROPHOBLAST CELL PREPARATIONS

CROSS-REFERENCE TO RELATED APPLICATIONS

This application was filed pursuant to 35 USC §371 as a national phase of PCT/CA99/00867, filed Sep. 23, 1999, which claims the benefit of U.S. patent application Ser. No. 60/101,483, filed Sep. 23, 1998.

FIELD OF THE INVENTION

The invention relates to trophoblast cell preparations and uses of the cell preparations.

BACKGROUND OF THE INVENTION

In mammals, the earliest developmental decision specifies the trophoblast cell lineage. In mice, this lineage appears at the blastocyst stage as the trophectoderm, a sphere of epithelial cells surrounding the inner cell mass (ICM) and the blastocoel. After implantation, the ICM gives rise to the embryo proper and some extraembryonic membranes. However, the trophectoderm is exclusively restricted to form the fetal portion of the placenta and the trophoblast giant cells. The polar trophectoderm (the subset of trophectoderm in direct contact with the ICM) maintains a proliferative capacity and gives rise to the extraembryonic ectoderm (ExE), the ectoplacental cone (EPC), and secondary giant cells of the early conceptus (1). The rest of the trophectoderm ceases to proliferate and becomes primary giant cells. Studies in primary culture and chimeric mice have suggested that stem cells exist in the extraembryonic ectoderm which contribute descendants to the EPC and the polyploid giant cells (2). Further evidence indicated that maintenance of these stem cell-like characteristics was dependent on signals from the ICM and later from the epiblast (3), since diploid trophoblast cells transformed into giant cells when removed from the embryonic environment (4). However, the nature of the embryo-derived signal was not known and all attempts at routine long-term culture of mouse trophoblast stem cells have been unsuccessful.

Expression and functional analyses indicated that Fgf4 and Fgfr2 may be involved in trophoblast proliferation (5, 6, 7). The reciprocal expression domains of Fgfr2 and Fgf4 suggested that the trophoblast could be a target tissue for an embryonic FGF signal. Fgfr2-null and Fgf4-null mice show similar peri-implantation lethal phenotypes (6, 7). This may result from defects in the ICM and its endoderm derivatives. However, it is also consistent with the possibility that FGF4 acts on the trophoblast through FGFR2 to maintain a proliferating population of trophoblast cells. Support for this latter possibility is provided by recent studies showing that inhibiting FGF signaling blocked cell division in both the ICM and trophectoderm (8).

SUMMARY OF THE INVENTION

The present inventors have found that FGF4 can promote sustained proliferation of primary cultures of diploid trophoblast cells and it permits isolation of stable FGF4-dependent mouse trophoblast stem (TS) cell lines from both the ExE of 6.5 dpc embryos and the trophectoderm of 3.5 dpc blastocysts. TS cell lines expressed many diploid trophoblast markers and retained the capacity to differentiate into other trophoblast subtypes in vitro upon removal of FGF4. Most importantly, when these stem cells were introduced into chimeras they exclusively contributed to all trophoblast subtypes in vivo. Availability of trophoblast stem cell lines opens up new possibilities for understanding the genetic regulation of placental development and placental insufficiencies and modulating the same. The cell lines also enable the treatment of placental insufficiencies by pharmacological intervention or gene-based therapy.

Broadly stated, the present invention relates to a stable pluripotent trophoblast stem (TS) cell line. In particular, the invention relates to a purified preparation of trophoblast stem cells which (i) are capable of indefinite proliferation in vitro in an undifferentiated state; and (ii) are capable of differentiation into cells of the trophoblast lineage in vivo. The preparation of trophoblast stem cells is also characterized by expression of genetic markers of diploid trophoblast stem cells.

A trophoblast stem cell preparation of the invention may be induced to differentiate into cells of the trophoblast lineage in vitro or in vivo. The invention therefore also relates to a purified trophoblast stem cell preparation of the invention (preferably cultured in vitro) induced to differentiate into cells of the trophoblast lineage. This differentiated cell preparation is characterized by expression of genetic markers of trophoblast cell lineages (e.g. diploid trophoblast cells of the ectoplacental cone (EPC), and the secondary giant cells of the early conceptus). In an embodiment of the invention a purified trophoblast cell preparation comprises cells of the trophoblast lineage including diploid trophoblast cells.

A cell preparation of the invention may be derived from or comprised of cells that have been genetically modified either in nature or by genetic engineering techniques in vivo or in vitro.

Cell preparations or cell lines of the invention can be modified by introducing mutations into genes in the cells or by introducing transgenes into the cells. Insertion or deletion mutations may be introduced in a cell using standard techniques. A transgene may be introduced into cells via conventional techniques such as calcium phosphate or calcium chloride co-precipitation, DEAE-dextran-mediated transfection, lipofection, electroporation, or microinjection. Suitable methods for transforming and transfecting cells can be found in Sambrook et al. (Molecular Cloning: A Laboratory Manual, 2nd Edition, Cold Spring Harbor Laboratory press (1989)), and other laboratory textbooks. By way of example, a transgene may be introduced into cells using an appropriate expression vector including but not limited to cosmids, plasmids, or modified viruses (e.g. replication defective retroviruses, adenoviruses and adeno-associated viruses). Transfection is easily and efficiently obtained using standard methods including culturing the cells on a monolayer of virus-producing cells (Van der Putten, supra; Stewart et al. (1987) EMBO J. 6:383–388).

A gene encoding a selectable marker may be integrated into cells of a cell preparation of the invention. For example, a gene which encodes a protein such as β-galactosidase, chloramphenicol acetyltransferase, firefly luciferase, or a fluorescent protein marker may be integrated into the cells. Examples of fluorescent protein markers are the Green Fluorescent Protein (GFP) from the jellyfish A. victoria, or a variant thereof that retains its fluorescent properties when expressed in vertebrate cells. (Examples of GFP variants include a variant of GFP having a Ser65Thr mutation of GFP (S65T) that has longer wavelengths of excitation and emission, 490 nm and 510 nm, respectively, compared to wild-type GFP (400 nm and 475 nm): a blue fluorescent variant of GFP (e.g. N66H-GFP) (Heim et al. Proc. Natl. Acad. Sci. 91:12501, 1994). MmGFP (M. Zernicka-Goetz et al, Development 124:1133–1137, 1997), enhanced GFP ("EGFP") (Okabe, M. et al. FEBS Letters 407:313–319, 1997; Clontech Palo Alto, Calif.), EGFP which has a Phe to Leu mutation at position 64 resulting in the increased stability of the protein at 37° C. and a Ser to Thr mutation at position 65 resulting in an increased fluorescence, and, EGFP commercially available from Clontech incorporating a humanised codon usage rendering it "less foreign" to mammalian transcriptional machinery and ensuring maximal gene expression.)

The invention also relates to a method for producing a purified trophoblast stem (TS) cell preparation i.e. a cell line, comprising the steps of culturing early postimplantation trophoblast cells or cells of a blastocyst, preferably from the trophectoderm on a feeder layer (e.g. a fibroblast layer or a medium conditioned by fibroblasts) in the presence of FGF4 and a co-factor. The method may additionally comprise inducing differentiation of the trophoblast stem cells by removing the FGF4, the co-factor, or the feeder layer. In an embodiment of the invention, the method comprises isolating a blastocyst, culturing the blastocyst on a fibroblast layer in the presence of FGF4 and a co-factor, removing a blastocyst outgrowth and dissociating the outgrowth, selecting flat colonies i,e. epithelial-like cells, and culturing the colonies. The invention also contemplates trophoblast cell preparations or lines derived at all stages of development under the same culture conditions.

The term "blastocyst" used herein refers to the structure during early embryonic development comprising an inner cluster of cells, the inner cell mass (ICM), which gives rise to the embryo, and an outer layer, the trophectoderm, which gives rise to extra-embryonic tissues. Preferably, cells from the trophectoderm of a 3.5 dpc blasotocyst are used in the method of the invention. The term "postimplantation trophoblasts" used herein refers to cells derived from extraembryonic extoderm (ExE) cells preferably isolated from 6.5 days post coitum conceptuses. The term "epithelial-like cells" refers to the flat colonies obtained after dissociation of a blastocyst outgrowth and which are like the cells which sometimes appear during the isolation of embryonic stem cells from blastocysts as described in B. Hogan et al (10).

The blastocysts or early postimplantation trophoblasts may be derived or isolated from any mammalian or marsupial species including but not limited to rodents (e.g. mouse, rat, hamster, etc.), rabbits, sheep, goats, pigs, cattle, primates, and humans are preferred. Mutant or transgenic blastocysts and postimplantation trophoblasts may be used to prepare a cell preparation or cell line of the invention. For example, a cell preparation or cell line of the invention may be derived from a Fgf4 or Errβ mutant blastocyst. Cells used to prepare a cell preparation or cell line of the invention can be engineered to contain a selectable marker or they may be genetically altered using techniques well known in the art.

The cells derived from a blastocyst or postimplantation trophoblast cells are cultured on a feeder layer. The feeder layer may be a confluent fibroblast layer, preferably primary mouse embryonic fibroblast (EMFI) cells. Embryonic fibroblasts may be obtained from 12 day old fetuses from outbred mice, but other strains may be used as an alternative. STO cells (i.e. a permanent line of irradiated mouse fibroblasts) can also be used as a feeder layer. The feeder layer may also comprise medium conditioned by primary embryonic fibroblast cells.

Cells from a blastocyst or early postimplantation trophoblast cells are preferably cultured in medium comprising RPMI 1640 with 20% fetal bovine serum, sodium pyruvate, β-mercaptoethanol, L-glutamine, and penicillin/streptomycin. The FGF4 used in the method of the invention may be recombinant FGF4 (preferably recombinant human FGF4) which may be produced using standard recombinant techniques or it may be obtained from commercial sources (e.g. Sigma). The co-factor used in the method of the invention is preferably heparin. Once established the cell lines may be grown on a feeder layer such as a fibroblast layer (e.g. EMFI cells) or in a conditioned medium prepared from a fibroblast layer (See for example the medium described in note 13, page 15).

Cells from the cell preparations may be introduced into a blastocyst or aggregated with an early stage embryo to produce chimeric conceptuses. A chimeric conceptus may be allowed to grow to term, or sacrificed during gestation to observe the contribution of the stem cell line. In an embodiment, the invention provides a chimeric placenta wherein the trophoblast lineage is repopulated by cells from a cell preparation of the invention. The conceptuses and placenta can be engineered to carry selectable markers or genetic alterations. Cell lines can be derived from the chimeric conceptuses and placenta. Therefore, the invention further provides a chimeric conceptus, differentiated trophoblast cells, mutant trophoblast stem cells, or a chimeric placenta derived from a purified preparation of the invention.

The cell preparations, chimeric conceptuses, and chimeric placentas may be used to screen for potential therapeutics that modulate trophoblast development or activity e.g. Invasion or proliferation. In particular, the cell preparations, chimeric embryos, or chimeric placenta may be subjected to a test substance, and the effect of the test substance may be compared to a control (e.g. in the absence of the substance) to determine if the test substance modulates trophoblast development or activity. Cell preparations of the invention derived from mouse mutants can be used to identify genes and substances that are important for the trophoblast cell lineage, and in vitro differentiation of mutant cell preparations can identify genes and substances important for selected trophoblast subtypes. Selected substances may be useful in regulating trophoblasts in vivo and they may be used to treat various conditions requiring regulation of trophoblast development or activity such as the conditions described below.

The cell preparations of the invention may be transplanted into animals to treat specific conditions requiring modulation of trophoblast development or activity. For example, the cell preparations may be used to prolong fetal survival in conditions of placental insufficiency, or to reduce uncontrolled trophoblast invasion and abnormal trophoblast growth associated with conditions such as hydatiform mole and choriocarcinoma. The cell preparations may be used for therapeutic treatment of placental defects in humans by transplantation of the cell preparations at any stage of pregnancy to generate chimeric placenta.

The cell preparations may be used to prepare model systems of disease for conditions such as precclampsia, hydatiform mole, or choriocarcinoma.

The cell preparations or cell lines of the invention can be used to produce growth factors, hormones, etc. relevant to human placenta. The cell preparations or cell lines of the invention can also be used to produce therapeutics such as human Chorionic Gonadotropin (hCG).

The cell preparations or cell lines of the invention can be used to screen for genes expressed in or essential for trophoblast differentiation. Screening methods that can be used include Representational Difference Analysis (RDA) or gene trapping with for example SA-lacZ (D. P. Hill and W. Wurst, Methods in Enzymology, 225: 664, 1993). Gene trapping can be used to induce dominant mutations (e.g. by deleting particular domains of the gene product) that affect differentiation or activity of trophoblast cells and allow the identification of genes expressed in or essential for trophoblast differentiation.

DESCRIPTION OF THE DRAWINGS

The invention will now be described in relation to the drawings in which:

FIGS. 1a–c. Trophoblast stem (TS) cell lines cultured in the presence and absence of FGF4 and EMFI-conditioned medium (EMFI-CM). (A) Differential interference contrast (DIC) micrograph (100×) of $TS_{3.5}$ cell colonies cultured on gelatinized glass in the presence of FGF4 and EMFI-CM (13). The cells grew as tight epithelial sheets with distinctly defined borders. Differentiated giant cells are indicated (arrows). (B) DIC micrograph (100×) of $TS_{3.5}$ cells cultured for 4 days on gelatinized glass in the absence of FGF4 and EMFI-CM. Large nuclei and dark, perinuclear deposits are characteristic of giant cells. Bar, 5 mm. (C) DNA content was analyzed by flow cytometric studies of cells stained with propidium iodide (PI) (14). TS cells were analyzed 0, 2, 4, and 6 days after the removal of FGF4 and EMFI-CM. Diploid (2N), tetraploid (4N), and octaploid (8N) DNA contents are indicated.

FIGS. 3a–e. TS cell chimeras generated by EGFP-$TS_{3.5}$ cell blastocyst injections. (A to D) A 6.5 dpc chimera. The intact conceptus revealed TS cell contributions to the extraembryonic ectoderm (ExE), a patch in the ectoplacental cone (EPC), and a few giant cells on Reichert's membrane (RM) (arrow) (A and B). Removal of RM and separation of the EPC from the ExE further illustrated the TS cell contributions to extraembryonic regions and not the epiblast (Epi) (C and D). (E to H) An 8.5 dpc chimera. A large contribution of TS cells to the placenta (Pl) was observed in the intact conceptus (E and F). A patch of EGFP-positive giant cells was also observed at the distal tip of the conceptus (enlarged in the inset). Removal of RM exposed the embryo proper (Emb) and the yolk sac (YS) which did not exhibit any TS cell contributions (G and H). (I and J) A 9.5 dpc chimera. The giant cell layer, yolk sac, and amnion have been removed. A substantial TS cell contribution was observed at the center of the placenta with a speckling of EGFP-positive cells emanating from it. This contribution is largely confined to the labyrinthine trophoblast. (K and L) A chimeric term placenta. Embryos were observed under partial bright-field (A, C, E, G, I, K) and dark-field optics (B, D, F, H, J, L). Green fluorescence was observed as described (26) and all photographs were taken with Kodak P1600 film at 1600 ASA.

DETAILED DESCRIPTION OF A PREFERRED EMBODIMENT

Figure 2A:
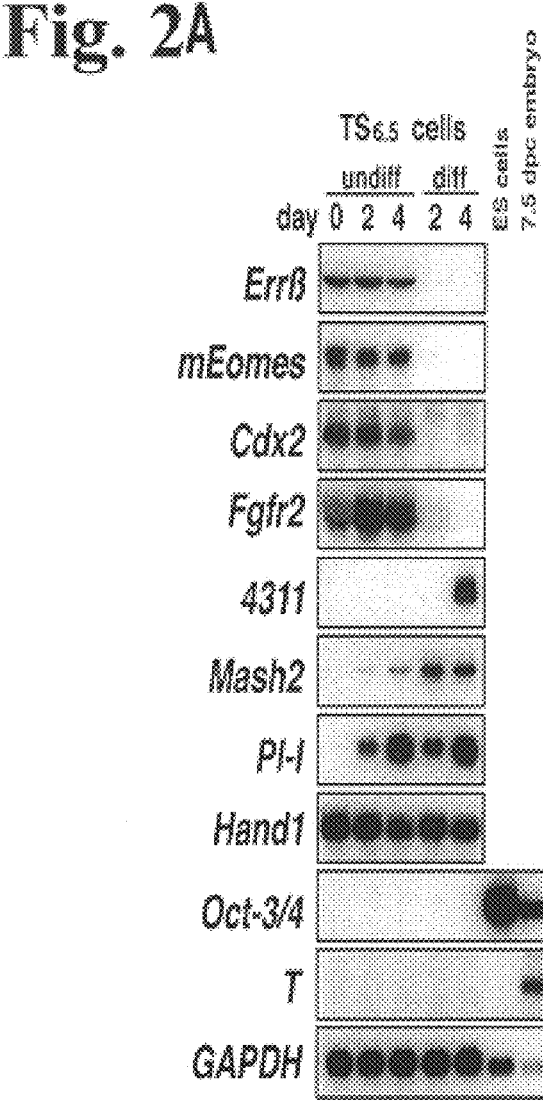
FIGS. 2a–b. RNA analysis of TS cell lines. (A) Northern blot analysis of gene expression in TS cell lines. TS cells were grown in 70% EMFI-CM and 30% TS medium supplemented with FGF4 and heparin for 2 days (13). The undifferentiated samples (undiff) were allowed to proliferate further in the same conditions for 0, 2, and 4 days (day 0, day 2, and day 4, respectively). The differentiated samples (diff) had FGF4, heparin, and EMFI-CM removed for 2 and 4 days (day 2 and day 4, respectively) and total RNA was prepared at each time point indicated. Total RNA (10 μg) from TS cells, undifferentiated ES cells, and 7.5 dpc embryos was fractionated on a 1% denaturing agarose gel and blotted onto a nylon membrane. Three blots were made for each cell line and sequentially probed/reprobed with antisense RNA probes as indicated (15). All three blots were finally reprobed with the GAPDH antisense RNA and confirmed to contain essentially equal amounts of RNA (only one blot is shown for each cell line). mEomes, mouse eomesodermin; T, brachyury (B) RT-PCR analysis of Hnf4 expression in the TS cells. From 0.5 μg of total RNA, first-strand cDNA was synthesized with (+) or without (−) reverse transcriptase. Primers specific for β-actin and Hnf4 were added in a single reaction tube to amplify both β-actin and Hnf4-specific fragments simultaneously (15). Amplification of Hnf4-specific fragments was never observed in TS cell samples. The predicted sizes of the β-actin and Hnf4 bands are 321 bp and 270 bp, respectively. Similar results were obtained from a $TS_{3.5}$ cell line.

TS cell lines were first derived from early postimplantation embryos. ExE cells were isolated from 6.5 dpc conceptuses as previously described (4), disaggregated by trypsin, and cultured on a feeder layer of primary mouse embryonic fibroblast (EMFI) cells in the presence of various combinations of growth factors (data not shown). The combination of FGF4 (25 ng/ml) and heparin (1 μg/ml) in TS cell medium (9) proved successful in allowing the passage of colonies with a tight epithelial morphology (FIG. 1A). Removal of either FGF4, heparin, or the EMFFI cells resulted in a rapid decline in proliferation with subsequent differentiation into a giant cell-like phenotype (FIG. 1B). Some giant cells also consistently appeared at the edges of colonies after each passage even under optimal conditions suggesting that a small percentage of the cells underwent spontaneous differentiation (FIG. 1A). Since the giant cells were relatively trypsin-resistant, they were left behind after each passage and so remained at a relatively constant level in the cultures.

Under the identical culture conditions used for isolating TS cell lines from ExE, cell lines were derived from 3.5 dpc blastocysts which exhibited a morphology and behavior indistinguishable from that of ExE-derived TS cell lines (12).The blastocyst-derived and ExE-derived lines are referred to as $TS_{3.5}$ and $TS_{6.5}$ cell lines, respectively, to distinguish their tissues of origin. Generation of $TS_{3.5}$ and $TS_{6.5}$ cell lines was efficient and reproducible; 58 clonal $TS_{3.5}$ cell lines were obtained from 91 blastocysts (64%) and 17 $TS_{6.5}$ cell lines from 39 ExEs of 6.5 dpc embryos (44%);

they were derived from different strain backgrounds (129/sv and ICR) and of both sexes Some of these TS cell lines were stably maintained for more than 50 passages over a period of more than six months with no apparent change in their morphology or viability.

To address the possibility that FGF4 stimulated the proliferation of TS cells indirectly by inducing the secretion of mitotic factors from the feeder cells, conditioned medium from EMFI cells (EMFI-CM) was prepared in the absence of FGF4. TS cells were maintained in an undifferentiated state on gelatin-coated plates in medium supplemented with 70% EMFI-CM and FGF4/heparin; lower concentrations of EMFI-CM were not effective (13). Leukemia inhibitory factor (LIF), the critical factor produced by EMFI cells that maintains ES cells undifferentiated, could not substitute for EMFI-CM even at five-times the concentration used in ES cell medium. These results suggest that a) EMFI cells secrete an unidentified factor(s) (EMFI-factor) that acts along with FGF4 to maintain the TS cells in a proliferative and undifferentiated state, b) secretion of this factor(s) is not a result of the addition of FGF4 to the media, and c) FGF4 acts directly on the TS cells.

Chromosome spreads from two TS cell lines passaged over 20 times revealed an apparently normal euploid karyotype. The ploidy of the stem cells and differentiated giant cells were determined by FACS analysis of cells stained with propidium iodide (14). The profile for cells maintained in EMFI-CM supplemented with FGF4heparin (13) revealed prominent peaks at 2N and 4N indicative of the G1 and G2/M DNA content of a diploid cell line (FIG. 1C). A small shoulder of higher ploidy cells (>4N) was also observed and was likely due to the presence of spontaneously differentiating giant cells in the culture. Upon removal of FGF4 and EMFI-CM a distinct 8N peak appeared within 4 days. The 2N peak was reduced and the 4N peak, which would include diploid G2/M cells and tetraploid G1 cells, increased in size. By day 6, cells of higher than 8N ploidy were seen in the analysis. These observations are consistent with the morphological differentiation of TS cells to giant cells.

Figure 2B:
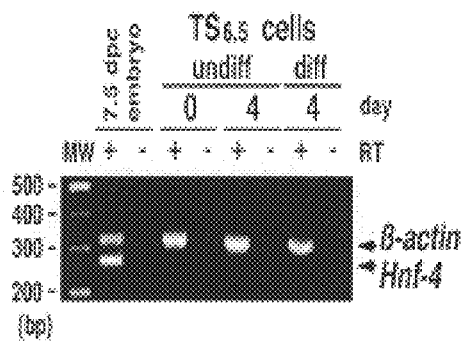

Several genetic markers were analyzed during stem cell and differentiative culture conditions to confirm the trophoblast identify of the $TS_{3.5}$ and $TS_{6.5}$ cell lines and characterize their differentiation in the absence of FGF4 (15). Markers of the diploid ExE were highly expressed in TS cells. Errβ, an orphan nuclear receptor, is specifically expressed in the ExE nearest to the extraembryonic-embryonic boundary at early postimplantation stages and later in the chorionic ectoderm (16). This gene was highly expressed in TS cells grown in the presence of FGF4 and 70% EMFI-CM, but was down-regulated when differentiation was induced by removing FGF4 and EMFI-CM (FIG. 2A). This was also the case for other genes known to be highly expressed in the ExE, such as Cdx2 (17), Fgfr2 (6), and the mouse homologue of eomesodermin (18) (FIG. 2A). In contrast to the ExE-specific genes, 4311, an EPC-specific gene (19), was not detected in the undifferentiated cells, but was induced 4 days after the removal of FGF4 and EMFI-CM. Mash2, encoding a basic helix-loop-helix (bHLH) transcription factor, has been shown to be required in diploid trophoblast cells of the EPC to allow development of the spongiotrophoblast layer (20). Consistent with this, Mash2 was upregulated in differentiating TS cells prior to the expression of 4311 (FIG. 2A). Mash2 transcripts were also progressively induced in TS cells cultured in stem cell conditions. *Placental lactogen*1 (Pl-1), a specific marker for giant cells (21), is progressively induced in cultures after removal of FGF4, consistent with the predicted increase in giant cell content. As observed for the Mash2 gene, the increasing expression of Pl-1 during stem cell culture conditions may reflect the presence of spontaneously differentiating cells that accumulate after each passage (FIG. 2A). Hand1, another bHLH transcription factor that is known to play an important role in the development of giant cells but is not expressed in the ExE (22), was detected throughout the culture periods analyzed regardless of the presence of FGF4 and EMFI-CM (FIG. 2A). Oct3/4, Brachyury, and Hnf4, genes specific for ICM/epiblast (23), mesoderm (24), and primitive endoderm (25), respectively, were not detected in TS cells (FIG. 2). Thus, these established cell lines conserve a gene expression profile largely characteristic of trophoblast cells in the ExE and they express distinctive markers of other trophoblast cell lineages upon differentiation.

The most definitive test for the trophoblast identity and stem cell capacity of TS cells is to investigate their potential to incorporate into trophoblast lineages in vivo. Rossant et al. (2) have shown that the cells isolated from the ExE of 6.5 dpc embryos can contribute to the EPC and giant cells when directly injected into blastocysts, despite temporal asynchrony between donor and host cells. To investigate the potency of TS cells to contribute to trophoblast lineages in vivo, chimeric embryos were made by the aggregation method (26) and blastocyst injection. A $TS_{3.5}$ and a $TS_{6.5}$ cell line were derived from B5/EGFP transgenic mice (27) that ubiquitously express enhanced-green fluorescent protein (EGFP, Clontech) in all embryonic and extraembryonic tissues. These lines were passaged more than 20 times (two months) before they were used for the chimera experiments. Chimeras were obtained from each cell line using both methods (Table 1). EGFP-positive cells were only observed in tissues of the trophoblast lineage in the 61 chimeric embryos analyzed (FIG. 3). TS cells contributed to the ExE, EPC, and giant cells, but were never observed in the epiblast, primitive endoderm, or other ICM-derived extraembryonic tissues, such as the allantois, yolk sac, and amnion (Table 2, FIG. 3). High contributions to chimeric placentae at term were also observed, indicating that these cells could functionally support fetal development (FIG. 3K, L). There was no significant difference between the EGFP-$TS_{3.5}$ and EGFP-$TS_{6.5}$ cell lines in their ability to contribute to trophoblast subtypes. However, blastocyst injections gave a higher frequency of chimeras than the aggregation method (Table 1). These results clearly show that TS cells retain the potency to differentiate into all trophoblast cell types in vivo despite being cultured in vitro for extended periods of time. Taken together with the results of the Northern analyses it was concluded that a stable pluripotent mouse trophoblast stem (TS) cell line was established.

Figures 4A, 4B:
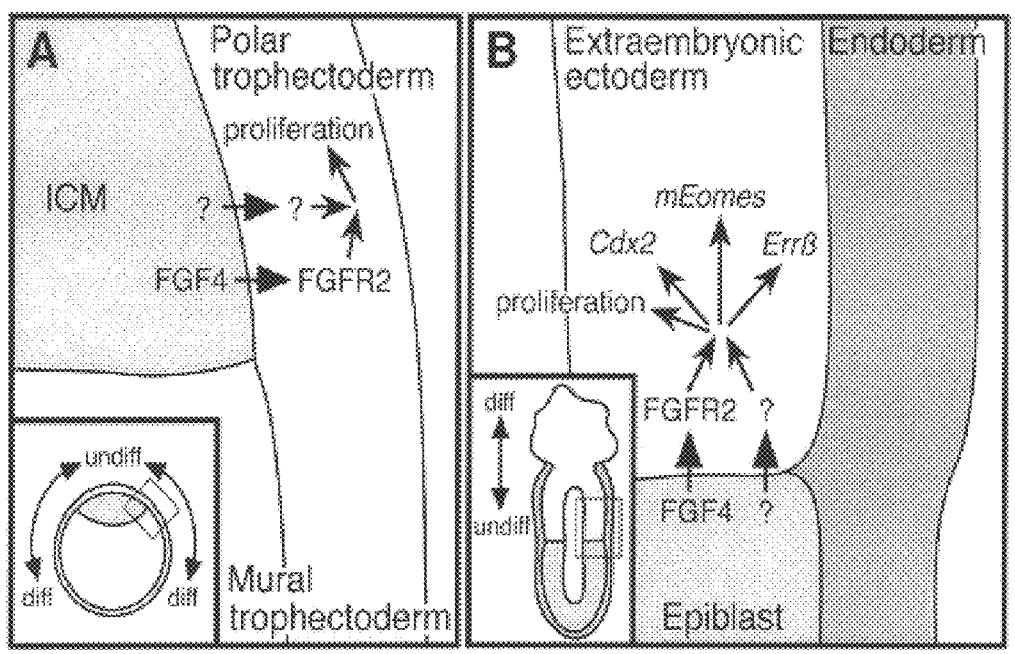
FIGS. 4a–b. A model for embryonic-trophoblast interactions and the maintenance of TS cells if) vivo. (A) A schematic drawing of a 3.5 dpc blastocyst (inset) emphasizing a region where the polar and mural trophectoderm meet with the ICM. FGF4 and at least one other unidentified factor produced in the ICM may signal to the overlying polar trophectoderm, maintaining it in a proliferative state. As the trophectoderm cells move away from the ICM to become mural trophectoderm, they cease to receive the ICM-derived signals and consequently differentiate. (B) A schematic drawing of a 6.5 dpc conceptus (inset) emphasizing the embryonic-extraembryonic boundary. Similar to the blastocyst scenario, this suggested that FGF4 and an unknown factor(s) from the epiblast signal to the extraembryonic ectoderm (ExE) and directly or indirectly mediate the expression of genes such as Errβ, Cdx2, and mEomes (eomesodermin). These signals maintain a trophoblast stem cell population in the ExE nearest to the epiblast. As trophoblast cells move away from the embryonic-extraembryonic border, they no longer receive the epiblast signals and initiate a differentiation pathway.

It has been proposed that the ExE is the first tissue to be formed from the polar trophectoderm and that it may act as a stem cell population that subsequently gives rise to the EPC which generates new secondary giant cells (2, 3). Successful derivation of TS cell lines expressing trophoblast markers from the ExE of 6.5 dpc embryos and 35 dpc blastocysts is consistent with this model. FGF4 produced by the ICM and later by the epiblast is one of the critical signals required for the maintenance of the proliferative undifferentiated state of ExE (FIG. 4). From the expression pattern and null phenotype of the Fgfr2 gene, this receptor tyrosine kinase is the best candidate to functionally receive the FGF4 signal in the trophoblast. This model predicts that the lethality observed in homozygous null mutants for both Fgf4 and Fgfr2 (6, 7) may in part be caused by the loss of the proliferating population of the ExE soon after implantation.

During normal implantation the blastocyst first adheres to the uterine wall through its mural trophectoderm at the abembryonic pole; however, Fgfr2 −/− blastocysts implanted randomly implying that the trophectoderm surrounding the embryo is not polarized. The components downstrean of the trophoblast FGF response are not known, but the T-box gene, mouse eomesodermin, and the caudal-related gene, Cdx2, are good candidates since they are expressed in the appropriate cells and members of these gene families have been shown to be regulated by FGF-signaling (28, 29). As trophoblast cells continue to proliferate and move distally from the ICM/epiblast, they cease to receive the mitotic and differentiation-inhibitory signals from the embryo proper. This would result in differentiation into EPC and finally to giant cells.

The above model makes a number of testable predictions about the involvement of FGF-signaling in trophoblast development. For example, the model predicts that TS cell lines could be derived from Fgf4, but not Fgfr2 mutant blastocysts. Establishing TS cell lines from other mouse mutants will reveal the genes essential for this stem cell lineage, while in vitro differentiation of mutant lines will identify genes important for other trophoblast subtypes. In summary, the establishment of FGF4-dependent TS cell lines from blastocysts and the ExE of 6.5 dpc embryos has revealed that a stem cell population exists within the trophoblast lineage for at least a 3-day window during early development and that the essential embryo-derived signals for trophoblast proliferation include FGF4. These cell lines are an invaluable tool to further dissect the function of genes and signaling pathways important to the development of the mammalian trophoblast lineage and its interactions with the embryo. The ability of wild type TS cells to make high contributions in chimeras indicates that these cells have the potential to rescue mutant embryos with placental defects. Such "TS cell rescue" analysis could be an alternative to the "tetraploid rescue" technique (27) currently used. Finally, obtaining similar trophoblast stem cell lines from human embryos opens up new avenues to future cell-based therapies for placental insufficiencies.

TABLE 1

Frequency of obtaining implanted embryos and chimeric conceptuses from diploid aggregations and blastocyst injections of EGFP-TS$_{3.5}$ and EGFP-TS$_{6.5}$ cell lines. Significant differences were not observed between the two cell lines analyzed. However, blastocyst injections (blast.inj.) yielded a higher percentage of implanted embryos and a higher percentage of chimeras than diploid aggregations (dip.agg.). TS cells were not viable in the culture medium (KSOM) routinely used for diploid aggregations with embryonic stem cells. Altering the aggregation medium to 90% KSOM, 10% FBS, 25 ng/ml FGF4, and 1 mg/ml heparin increased the viability of the TS cells, but decreased the fitness of the embryos. Consequently, blastocyst injections of TS cells were routinely performed since it avoids the overnight culture required for aggregations.

| Cell line (technique) | No. Transferred | No. Embryos (% transferred) | No. Chimeras (% embryos) |
|---|---|---|---|
| EGFP-TS$_{3.5}$ (blast.inj.) | 176 | 100 (57%) | 47 (47%) |
| EGFP-TS$_{6.5}$ (blast.inj.) | 42 | 21 (50%) | 9 (43%) |
| EGFP-TS$_{3.5}$ (dip.agg.) | 177 | 29 (16%) | 4 (14%) |
| EGFP-TS$_{6.5}$ (dip.agg.) | 112 | 17 (15%) | 1 (6%) |
| Total | 507 | 167 (33%) | 61 (37%) |

TABLE 2

Location of TS cell contributions. ExE, extraembryonic ectoderm; EPC, ectoplacental cone; GC, giant cells; ChE, chorionic ectoderm; Spong, spongiotrophoblast; Lab, labyrinthine trophoblast.

| Stage | No. Chimeras | Cell Type |
|---|---|---|
| 6.5 dpc (n = 15) | 4 | ExE, EPC, GC |
|  | 3 | EPC, GC |
|  | 4 | ExE, EPC |
|  | 1 | Exe |
|  | 1 | EPC |
|  | 2 | GC |
| 7.5 dpc (n = 2) | 1 | EPC, GC |
|  | 1 | GC |
| 8.5 dpc (n = 11) | 1 | ChE, EPC, GC |
|  | 1 | EPC, GC |
|  | 2 | ChE, GC |
|  | 1 | ChE, EPC |
|  | 4 | EPC |
|  | 2 | GC |
| 9.5 dpc (n = 8) | 1 | ChE, EPC, GC |
|  | 1 | EPC, GC |
|  | 1 | ChE, GC |
|  | 2 | EPC |
|  | 3 | GC |
| 10.5 dpc (n = 9) | 1 | Lab, Spong, GC |
|  | 2 | Spong, GC |
|  | 1 | Lab, Spong |
|  | 2 | Spong |
|  | 3 | GC |
| 11.5 dpc (n = 8) | 2 | Lab, Spong, GC |
|  | 2 | Lab, Spong |
|  | 1 | Spong, GC |
|  | 3 | Spong |
| 18,5 dpc (n = 8) | 1 | Lab, Spong, GC |
|  | 5 | Lab, Spong |
|  | 2 | Spong |

While the present invention has been described with reference to what is presently coincided to be a preferred embodiment, it is to be understood that the invention is not limited to the disclosed embodiment. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

References and Notes

1. J. Rossaint, in *Experimental Approaches to Mammalain Embryonic Development*, J. Rossant and R. A. Pederson. Eds (Cambridge Univ. Press, London, 1986), pp. 97–120; J. Rossant, *Sem. Dev. Biol.* 6, 237 (1995).
2. J. Rossant, R. L. Gardner, H. L. Alexandre, *J. Embryol. Exp. Morpihol.* 48, 239 (1978); M. H. Johnson and J. Rossant, ibid. 61, 103 (1981).
3. R. L. Gardner and M. H. Johnson, ibid. 28,279 (1972); J. Rossant and W. Iamura-Lis. ibid. 62, 217 (1981); E. B. ligren, Placenta 4, 307 (1983).
4. J. Rossant and L. Ofer, *J. Embryol. Exp. Morphol.* 39, 183 (1977); E. B. llgren, ibid. 62,183 (1981).
5. L. Niswander and G. R. Martin, *Development* 114, 755 (1992); D. A. Rappolee, C. Basilico, Y. Patel, Z. Werb, ibid. 120, 2259 (1994).
6. A. Orr-Urtreger et al., *Dev. Biol.* 158, 475 (1993); E. Arnan, R. Haffner-Krausz, Y. Chen, J. K. Heath, P. Lonai, *Proc. Natl Acad. Sci. U.S.A.* 95, 5082 (1998); J. Partanen and J. Rossant, unpublished data.
7. B. Feldman, W. Poueymirou, V. E. Papaioanriou, T. M. DeChiara, M. Goldfarb, Science 267, 246 (1995).
8. N. Chai et al., *Dev. Biol.* 198, 105 (1998).
9. TS cell medium is RPMI 1640 supplemented with 20% fetal bovine serum (HyClone), sodium pyruvate (1 mM, GibcoBRL), β-mercaptoethanol (100 μM, Sigma), L-glutamine (2 mM, GibcoBRL), and penicillin/ streptomycin (50 μg/ml each). Human recombinant FGF4 (25 ng/ml, Sigma) and heparin (1 μg/ml) were added to aliquots of TS cell medium and used immediately.
10. B. Hogan, R. Beddington, F. Costantini, E. Lacy, *Manipulating the Mouse Embryo* (Cold Spring Harbor Laboratory Press, Cold Spring Harbor, N.Y., ed. 2, 1994), pp. 265–272; E. J. Robertson, in *Teratocarcinomas and Embryonic Stem Cells*, E. J. Robertson, Ed. (IRL Press, Oxford, 1987), pp. 71–112.
11. J.-E. Fléchon, S. Laurie, E. Notarianni, *Placenta* 16, 643 (1995).
12. $TS_{3.5}$ cell lines were obtained using similar techniques for ES cell line derivation (10). Briefly, 3.5 dpc blastocysts were individually plated into 4-well plates on EMFI cells and cultured in TS media with FGF4 and heparin (9). The medium was changed after two days and the blastocyst outgrowth was trypsinized on the third day. On day 5 or 6, flat colonies, referred to as "epithelial-like cells" in (10). were picked and passaged. Once established, the cell lines were grown without EMFI cells, but in the presence of EMFI conditioned medium (13). Under the current culture conditions ES cell colonies were not observed.
13. Conditioned medium from EMFI cells (EMFI-CM) was prepared by incubating TS medium (9) without FGF4 or heparin on confluent plates of mitomycin-treated EMFI cells for 72 hours. The conditioned medium was filtered (0.45 μm) and stored at −20° C. Established TS cell lines were routinely cultured in 70% EMFI-CM, 30% TS medium, 25 ng/ml hrFGF4 and 1 μg/ml heparin on gelatin-coated plates. The medium was changed every two days and the cells were passaged (1 in 25) every four days or at 80%–90% confluency.
14. TS cells were grown in the absence of EMFI cells (13) and collected by cell scraping at 0, 2, 4, and 6 days after the removal of FGF4, heparin, and EMFI-CM. The cells were fixed and stained with propidium iodide (Molecular Probes) as described [Z. Darzynkiewicz and G. Juan, in Current Protocols in Cytometry (John Wiley & Sons, Inc., New York, 1997), pp. 7.5.2–7.5.3]. Cell fluorescence was measured by a flow cytometry with an argon ion laser (488 nm). The data was analyzed with Coulter EXPO Cytometer Software version 2.0 by Applied Cytometry Systems, 1998.
15. Total RNA was prepared from cells and embryos with TRIzol (GibcoBRL) according to the manufacturer's instructions. Northern blotting was performed by a standard protocol. Antisense RNA probes for Errβ(16), eomesodermin (18), Cdx2 [E. Suh, L. Chen, J. Taylor, P. G. Traber, *Mol Cell. Biol.* 14, 7340 (1994)], Fgfr2, Mash2 (20), 4311 (19), Handl (22), Pl-1 [P. Colosi, F. Talamantes, D. I. H. Linzer, *Mol. Endocrinol.* 1, 767 (1987)], Oct-3/4 (23), Brachyury (24), and GAPDH [P. Fort et al., *Nucleic Acids Res.* 13, 1431 (1985)] were labeled with either [$\alpha$-$^{32}$P]UTP or DIG-11-UTP (Boehringer Mannheim) by using Strip-EZ RNA kit (Ambion). Blots were hybridized overnight at 65° C. in NorthernMax Prehybridization/hybridization Buffer (Ambion) and were finally washed in 0.1×SSC/0.1% SDS at 65° C. DIG-labeled probes were detected with the DIG Luminescent Detection Kit (Boehringer Mannheim). Removal of hybridized RNA probes was performed with the Strip-EZ RNA kit (Ambion) according to manufacturer's recommendations. To assess the expression of Hnf4 in the TS cell lines, first strand cDNA synthesized from 0.5 μg total RNA of TS cells and 7.5 dpc embryos with random hexamers was subjected to 35 cycles of PCR (62° C. annealing temperature) by using 0.2 μM each of Hnf4-specific primers (5'-CACGTCCCCATCTGAAGGTG-3' and 5'-CTTCCTTCTTCATGCCAGCCC-3') and 0.1 μM each of β-actin-specific primers (5'-GACAACGGCTCCGGCATGTGCAAAG-3' and 5'-TTCACGGTTGGCCTTAGGGTTCAG-3'). The primer sequences were adapted from D. loannis et al., *Development* 125, 1529 (1998).
16. K. Pettersson et al., *Mech. Dev.* 54, 211 (1996); J. Luo et al., *Nature* 388, 778 (1997).
17. F. Beck, T. Erler, A. Russell, R. James, *Dev. Dyn.* 204, 219 (1995).
18. B. G. Ciruna and J. Rossant, Mech. *Dev.* 81, 199 (1999).
19. K. R. Lescisin, S. Varmuza, J. Rossant, *Genes Dev.* 2, 1639 (1988).
20. F. Guillemot, A. Nagy, A. Auerbach, J. Rossant. A. L. Joyner, *Nature* 371, 333 (1994); M. Tanaka, M. Gertsenstein. J. Rossant, A. Nagy, *Dev. Biol.* 190, 55 (1997).
21. T. N. Faria. L. Ogreni. F. TalamanIes, D. I. Linzer. M. J. Soares, *Biol. Reprod.* 44, 327 (1991).
22. J. C. Cross et al., *Development* 121, 2513 (1995); P. Riley. L. Anson-Cartwright, J. C. Cross. *Nat. Genet.* 18, 271 (1998).
23. S. L. Palmieri, W. Peter, H. Hess, H. R. Schöler. *Dev. Biol.* 166, 259 (1994); H. R. Schöler. G. R. Dressier, R. Balling. H. Rohdewohld, P. Gruss. *EMBO J.* 9, 2185 (1990).
24. D. G. Wilkinson, S. Bhatt, B. G. Herrmann, *Nature* 343, 657 (1990).
25. S. A. Duncan et al., *Proc. Natl. Acad. Sci. U.S.A.* 91, 7598 (1994).
26. A. Nagy and J. Rossant, in *Gene Targeting*, A. L. Joyner Ed. (IRL Press. Oxford, 1993), pp. 147–180; S. A. Wood, 26. N. D. Allen, J. Rossant, A. Auerbach, A. Nagy, *Nature* 365, 87 (1993).
27. A.-K. Hadjantonakis, M. Gertsenstein, I. Ikawa, M. Okabe, A. Nagy, *Mech Dev.* 1998 August;76(1–2):79–90.
28. K. J. P. Griffin, S. L. Amacher, C. B. Kimmel, D. Kimelman, *Development* 125, 3379 (1998); K. Griffin, R. Patient, N. Holder, ibid. 121, 2983 (1995).
29. M. E. Pownall, H. V. Isaacs, J. M. Slack, *Curr. Biol.* 8, 673 (1998); H. V. Isaacs, M. E. Pownall, J. M. Slack, *EMBO J.* 17, 3413 (1998).

We claim:

1. An isolated preparation of mouse trophoblast stem cells which (i) are capable of indefinite proliferation in vitro in an undifferentiated state; (ii) are capable of differentiation into cells of the trophoblast lineage in vivo, and (iii) are diploid trophoblast cells.

2. An isolated preparation as claimed in claim 1 wherein the cells are characterized by expression of the genetic markers Errβ, Cdx2 and Fgfr2.

3. The isolated preparation according to claim 1 which is derived from or comprised of cells that have been genetically modified by genetic engineering techniques.

4. An isolated cell preparation as claimed in claim 3 modified by introducing mutations into genes in the cells or by introducing transgenes into the cells.

5. A method for producing a preparation of mouse trophoblast stem cells as claimed in claim 1 comprising culturing early postimplantation trophoblast cells or cells of a blastocyst from a mouse on a feeder laser in the presence of exogenous FGF4 and heparin, said feeder layer selected from the group consisting of fibroblasts or medium conditioned by fibroblasts.

6. A method for producing differentiated cells of trophoblast lineages comprising culturing early postimplantation trophoblast cells or cells of a blastocyst from a mouse as claimed in claim 5 and inducing differentiation of the stern cells to cells of trophoblast lineages by removing the FGF4, the heparin, or the feeder layer.

7. A method as claimed in claim 5 wherein the early postimplantation trophoblast cells or cells of a blastocyst are transgenic.

8. A method as claimed in claim 5 wherein the feeder layer is a confluent fibroblast layer or a medium conditioned by primary embryonic fibroblast cells.

9. A method as claimed in claim 5 wherein the feeder layer comprises primary mouse embryonic fibroblast (EMFI) cells or STO cells.

10. A method as claimed in claim 5 wherein the FGF4 is recombinant FGF4.

11. A method for producing chimeric conceptuses or placenta comprising the steps of producing a preparation of mouse trophoblast stem cells as claimed in claim 5 and further comprising the step of introducing cells frown the preparation into a non-human blastocyst or aggregating the cells with an early stage non-human embryo to produce chimeric conceptuses or placenta.

12. A method as claimed in claim 11 wherein the chimeric conceptuses or placenta are engineered to carry selectable markers or genetic alterations.

13. A method as claimed in claim 11 wherein cell lines are derived from the chimeric conceptuses or chimeric placenta.

14. A method for producing a preparation of mouse trophoblast stem cells as claimed in claim 1 comprising:
    (a) isolating extraembryonic cells from embryos or blastocysts from a mouse;
    (b) culturing the extraembryonic cells on a feeder layer in the presence of exogenous FGF4 and heparin to thereby obtain an isolated preparation of mouse trophoblast stem cells, said feeder layer selected from the group consisting of fibroblasts or medium conditioned by fibroblasts.

15. A method for producing differentiated cells of trophoblast lineages comprising culturing extraembryonic cells according to claim 14, and inducing differentiation of the stem cells to cells of trophoblast lineages by removing the FGF4, the heparin, or the feeder layer.

16. A method for screening for potential therapeutics that modulate trophoblast development or activity comprising subjecting an isolated preparation of mouse trophoblast stem cells which (i) are capable of indefinite proliferation in vitro in an undifferentiated state; (ii) are capable of differentiation into cells of the trophoblast lineage in vivo, and (iii) are diploid trophoblast cells, to a test substance, and comparing the effect of the test substance to a control to determine if the test substance modulates trophoblast development or activity.

* * * * *